United States Patent
Häberlein et al.

(10) Patent No.: US 6,752,989 B1
(45) Date of Patent: Jun. 22, 2004

(54) TOOTH SURFACE TREATMENT AGENT

(75) Inventors: Ingo Häberlein, Weilheim (DE);
Thomas Luchterhandt, Krailling (DE);
Reinhold Hecht, Inning-Buch (DE);
Oliver Frey, Gauting-Königswiesen (DE)

(73) Assignee: 3M ESPE AG, Seefeld (DE)

( * ) Notice: Subject to any disclaimer, the term of this patent is extended or adjusted under 35 U.S.C. 154(b) by 187 days.

(21) Appl. No.: 10/030,942

(22) PCT Filed: Nov. 17, 2000

(86) PCT No.: PCT/EP00/11187

§ 371 (c)(1),
(2), (4) Date: Jan. 15, 2002

(87) PCT Pub. No.: WO01/37787

PCT Pub. Date: May 31, 2001

(30) Foreign Application Priority Data

Nov. 19, 1999 (DE) .......................... 199 55 746

(51) Int. Cl.[7] .............................. A61K 38/48
(52) U.S. Cl. .................................. 424/94.67
(58) Field of Search ..................... 424/94.67

(56) References Cited

U.S. PATENT DOCUMENTS 5,762,502 A 6/1998 Bahn et al.

OTHER PUBLICATIONS

Jiro Tanaka, et al., "Application of Root Canal Cleaning Agents having Dissolving Abilities of Collagen to the Surface Treatment for Enhanced Bonding of Resin to Dentin" Dental Materials Journal, vol. 12, pp. 196–208, 1993.

A. Zach, et al., "Quantitative evaluation of the influence of dequalinum acetate and sodium hypochlorite on human dentition" Department of Endodontics, The Hebrew University, May 1983.

Yohsuke Taire, et al., "A Study on Cytochrome c Oxidoreductase for Bonding a Tri–n–butylborane–Initiated Luting Agent to Dentin" Department of Fixed Prosthodontics, Nagasaki University School of Dentistry, 1999, pp. 697–699.

V. I. Deribas, et al., "Treatment of dental caries—comprises filling the cleaned cavity with a mixture of immoblilised protease and gal, applying a temporary filling for 24 hours, and removing the remains of affected dentine next day" Sibe Cytology Genetics Inst., 1994 (with English abstract).

John Gwinnett, et al., "Quantitative contribution of the collagen network in dentin hybridization" American Journal of Dentistry, Aug. 1996.

P. Coli, et al., "In vitro dentin pretreatment: Surface roughness and adhesive shear bond strength" Eur. J. Oral Science, 1999.

A. Bahn, et al., Enzymatic Removal of the Smear Layer Journal of Dental Research, vol. 74 (Special Issue).

*Primary Examiner*—Jean C. Witz
(74) *Attorney, Agent, or Firm*—Crowell & Moring LLP

(57) ABSTRACT

The invention concerns surface treatment agents for hard tissue, including at least one enzyme and an agent inhibiting the enzyme activity, whereby the surface treatment agent remains on the hard tissue during the application.

10 Claims, 1 Drawing Sheet

TOOTH SURFACE TREATMENT AGENT

The present invention concerns a process for improving the adhesive fastening of dental materials on the dental hard substance by modifying the collagen layer present after preparation or etching.

The following steps are performed by the treatment provider for fastening dental materials on the prepared dental hard substance according to the current state of the art:

1. Slightly etching the overall dental hard substance using an acid ("total etching technique").
2. Applying a so-called primer, which superficially penetrates into the dental hard substance.
3. Application of a so-called bonding, which together with the primer forms a hybrid layer.
4. Polymerization of the bonding (for example by irradiation with light and/or through a redox reaction).
5. Application of the dental material.

In order to diminish the number of components to be applied, the primer and the bonding—or also sealant—were combined into one component (so-called onebottle bonding products, for example Prime & Bond 2.1, Dentsply/Detray company, Dreieich, Germany). Nonetheless, the area must first be etched and rinsed in order to free the smear layer, which has arisen in connection with the preparation (and represents a mixture, which basically consists of hydroxyl apatite and collagen), from hydroxyl apatite so that subsequently the onebottle bonding product can be applied at least once and subsequently be polymerized before the dental material is used. References are found in the literature which question the efficiency of this easily applied adhesive (R. Frankenberger, N. Krämer, J. Sindel, Dtsch. Zahnärztl. Z (German Dentist Magazine), 51: 556–560 (1996). In particular, the lifetime of the adhesive connection declines sharply with this simplified procedure.

Another simplification of the procedure described above for the adhesive fastening of dental materials consists of combining the primer and etching agent into one component (so-called self-etching primers; for example, Etch & Prime 3.0, Degussa company; Clearfill-Liner Bond 2.0, Kuraray company, Osaka, Japan). These need only be applied and no longer need to be rinsed—so-called "modification of the smear layer." This is followed by either the bonding to be polymerized (for example, Clearfill Liner Bond 2.0, Kuraray company, Osaka) or at least a reticulation step for polymerization of the self-etching primer before the dental material can be used.

After the first step (etching the dental hard substance), a network of exposed collagen fibers is present on the dentine. After polymerization has taken place, a so-called hybrid layer arises by the subsequent application of the primer or the bond (onebottle variant), initiated by exposure to light and/or a redox reaction. This hybrid layer consists of collagen fibers, which, together with the hardened monomers of the primer and/or bond, form an interpenetrating network. According to current theory, this hybrid layer is chiefly responsible for the adhesion between the dental hard substance and the dental materials (N. Nakabayashi et al., J. Biomed. Mater. Res., 1982, 16, 265–273; R. L. Erikson, Am. J. Dent. 1989, 2, 117–123; D. H. Pashley, Trans. Acad. Dent. Mater., 1990, 3, 55–73; B. v. Meerbek, dissertation 1993, Catholic University of Louvain). Furthermore, the hybrid layer acts as an elastic "buffer" between dental hard substance and dental material, as the modulus of elasticity lies approximately between both materials. Overall the hybrid layer is thus a basic component, which decisively contributes to the success of the preparation and the health of the remaining dental hard substance.

There are also studies, which show that not-impregnated partial areas of the collagen layer weaken the connection between the dental hard substance and dental material and possibly lead to an accelerated weakening of this connection (J. D. Eick, Proc. Fin. Dent. Soc., 1992, 88 (First supplement), 225–242; N. Nakabayashi et al.; Dent. Mater., 1992, 8, 125–130).

In order to obtain a good hybrid layer on the dentine, a complete wetting of all collagen fibers and therewith the observation of and pedantic compliance with the manufacturer's specifications are necessary (B. v. Meerbek et al., Dtsch. Zahnärztl. Z. 1994, 49, 977–984). Wetting the collagen fibers with the various bonding materials is, however, dependent upon various factors, such as, for example, the thickness and dryness of the collagen layer, the fiber length and the hydrophilicity of the bonding monomer matrix. In addition, the proportion of collagen in the dental hard substance is different or variable according to the individual characteristics of the patient. Establishing a good adhesive connection is therewith an extremely technique- and substance-sensitive process in dental practice, which but seldom leads to predictable results (J. Perdigao et al., Dent. Mater., 1997, 13, 218–227; B. v. Meerbek et al., Philip Journal, 1997, 9–10, 313–315).

U.S. Pat. No. 5,762,502 describes a method where either the smear layer arising after preparation can be removed by treatment with metalloproteinases or collagenases (substituting of the etching step) or the exposed collagen can be completely removed by these enzymes following the etching.

The task of the invention consists of avoiding problems known from the state of the art and making an improved surface treatment agent for hard tissues available.

The object of the present invention is solved by making available a surface treatment agent for hard tissues, including at least one enzyme and an agent restricting the enzyme activity. By using the agent, this remains on the hard tissue, whereby the enzyme activity is restricted temporarily and/or locally.

As a function of the concrete embodiment, the surface treatment agent of the present invention is first formed by mixing the individual components, especially the enzyme and the agent restricting the enzyme activity, immediately before the application or while applying the individual components on the surface to be treated.

A non-definitive enumeration of features is introduced with the term "include" and "contain." The circumstance that the word "one" is used before naming a feature does not rule out that the features mentioned can be present several times in the sense of "at least one."

The surface treatment agents from the invention can, for example, be used in bonding formulations in combination with an activity-terminating mechanism so that the enzyme or enzymes can remain on the dental hard substance without damaging it.

The surface treatment agents from the invention have, among other things, the following advantages.

In contrast with the state of the art, the enzyme solution does not have to be separately applied and rinsed each time. This saves the dentist and the patient three additional steps (applying the enzyme solution, allowing it to act, and subsequent rinsing). The treatment is shortened and simplified (it is recognized that the complexity of the classic four-step bonding procedure very often led to mistakes and poor clinical results).

A further advantage in comparison with the state of the art is retention of the hybrid layer, which is important for sealing and for the adhesion on the dental hard substance, which also has an essential function as an elastic buffer between tooth and dental material. One must imagine that the structure of the layers of mineralized dentine-hybrid layer-bonding-dental material takes place through hardness gradients, where the hybrid layer has assumed basically a "mediator role."

Finally, there is no longer the danger with the surface treatment of the invention that, if the enzyme solution used is not completely rinsed off, it remains at least partially on the tooth and there damages the dental hard substance by degradation of the collagen present in the adjacent dentine, even under the applied bonding.

The fact that the juncture is in fact severely damaged when collagenase remains too long on the exposed dentine is shown in the present invention by the comparison examples and illustration 1.

The invention furthermore makes a method available where on the one hand the bonding procedure from the state of the art is simplified and shortened, and on the other a basic improvement of values of adhesion, technique sensitivity and flow behavior on the mineralized dentine surface is obtained while retaining the hybrid layer.

By pulverizing or modifying the collagen fibers by proteases, one obtains a more even and always identical configuration of the surfaces to be wetted. Since the diffusion resistance of the monomer molecules of the primer or bonding against pulverized or modified collagen fibers is considerably smaller, the formation of a good hybrid layer can take place more rapidly and completely. This results in an always identical and improved flow behavior, which consequently causes a complete wetting of the mineralized dentine surface and herewith also a lower sensitivity of the bonding technique. Consequently, this results in an improvement in the clinical safety of the entire filling with improved adhesion. Moreover, obtaining a hybrid layer with all its aforementioned advantages is guaranteed.

Through the use of the enzymes in accordance with the invention, the adhesion values of the filling materials to teeth or the bonding can be increased, and the standard deviation in the measurements can be reduced, owing to which it becomes possible to produce formulations, which deliver reproducible results.

A further advantage of the invention is the abbreviated process, which enables the use of enzymes directly in the bonding and sealing materials, and therewith aids the treating physician in possibly avoiding errors, and shortens the treatment time for the patient.

The invention will be described in greater detail below, whereby the term enzyme includes proteolytic enzymes as well as proteases.

Basically those proteases, which are capable of cutting up collagen fibers as they occur in dental hard substance and/or those which are capable of altering the collagen fibers such that these manifest an improved solubility behavior, can be used. All those enzymes, which can alter proteins proteolytically, are grouped under the term proteases. Peptidases, peptidyl peptidases, dipeptidases, dipeptidyl peptidases, oligopeptidases, proteinases, endopeptidases, and exopeptidases, for example, belong to the proteases. A classification of proteases can also take place with respect to amino acids or cofactors, which are involved in proteolytic catalysis. One thus differentiates between serine peptidases, cysteine peptidases, aspartate peptidases and metallopeptidases and their sub-categories. A current overview of proteolytically active enzymes is provided in A. J. Barrett, N. D. Rawlings, J. F. Woessner, *Handbook of Proteolytic Enzymes*, San Diego: Academic Press, 1998, which also mentions proteases, which could not previously be allocated to certain protease classes. The enumeration of the proteases of the invention is by way of example and is in no way to be understood as limiting in the sense of the invention. Usually proteases dispose over defined action sites. Thus only defined regions of collagen fibers are attacked according to the protease. Moreover, the activity of proteases can be selectively controlled over time, in contrast to which the chemical reaction of chemical agents continues until complete consumption.

Proteases can be used within the meaning of the invention individually or in combination with other proteases.

The following possibilities and their combinations chiefly come into consideration for the use of the enzymes:

In a separately applied conditioner which can be usually neutral, if need be also acidic or basic;

In a primer usually used for bondings;

In a self-etching primer;

In a so-called onebottle bond;

In a self-etching bonding, so-called onestep bond or also all-in-one adhesive.

In addition to enzymes, chemical agents can also be used, which can cut up proteins or make alterations in their structure. Examples are N-halogenated amines, hypochlorite, called $H_2O_2$.

The surface treatment agent furthermore contains if need be one or more substances selected from: Fillers, especially permanent fillers, colorants, flow modifiers, stabilizers, solvents, ion-emitting substances, bactericidally or antibiotically active substances, X-ray opacity-increasing compounds or further modifiers.

Suitable initiators include camphor quinone in combination with amines (aromatic amines), 1,2-diketones and (mono, bis and tris)-acyl phosphinoxides. Suitable radical-forming initiators are described in the literature (for example, J.-P. Fouassier, Photoinitiation, Photopolymerization and Photocuring), Munich, Vienna, New York: Hanser Publishers, 1995 or also J.-P. Fouassier, J. F. Rabek, ed., Radiation Curing in Polymer Science and Technology, Vol. II, London, New York: Elsevier Applied Science, 1993). They can be substances that can be activated by UV or visible light such as benzoin alkyl ether, benzil ketals, acyl phosphinoxides or aliphatic and aromatic 1,2-diketone compounds, for example, camphor quinone, whereby the catalytic activity can be accelerated through the addition of activators, such as tertiary amines or organic phosphites in an inherently known manner.

Peroxide/amine, peroxide/barbituric acid derivatives or peroxide/acids and the like, for example, are suitable initiator systems for triggering radical polymerization through a redox mechanism. When using such initiator systems, it is appropriate to keep an initiator (for example, peroxide) and a catalyst component (for example, amine) ready separately. The two components are then homogeneously mixed shortly before their application.

Polymerizable substances include in particular monofunctional or polyfunctional acrylates and methacrylates as they are described in EP-A-0 480 472. Functionalized monomers with end positioned acrylate or methacrylate groups, such as they are described in DE-A-2 312 559 and EP-A-0 219 058, can also be used. Alkyl(meth)acrylates, including cycloalkyl (meth)acrylates, aralkyl(meth)acrylates and 2-hydroxy alkyl (meth)acrylates, for example hydroxy propyl methacrylate, hydroxy ethyl methacrylate, isobornyl acrylate, isobornyl methacrylate, butyl glycol methacrylate, acetyl glycol methacrylate, triethylene glycol diemethacrylate, polyethylene glycol dimethacrylate, 2-phenyl ethyl methacrylate, 2-ethyl hexyl methacrylate, cyclohexyl methacrylate, lauryl methacrylate and hexane diol di(meth)acrylate are typical representatives of this compound class (DE-A-4 328 960). Long chain monomers, as they are described in U.S. Pat. No. 3,066,112, on the basis of bisphenol A and glycidyl methacrylate or their derivatives arising by the addition of isocyanates, can also be used. Bisphenyl-A-diethyloxy (meth)acrylate and bisphenol-A-dipropyloxy(meth)acrylate type compounds are also suitable. Furthermore, oligoethyxylated and oligopropylated bisphenol-A-diacrylic acid ester and bisphenol-A-dimethacrylic acid ester can find application. Moreover, the diacrylic and dimethylacrylic acid esters of bis(hydroxymethyl)-tricyclo[5.2.1.0$^{2,6}$]-decane and the diacrylic and dimethacrylic acid esters of the bis(hydroxymethyl)tricyclo[5.2.1.0$^{2,6}$] decane compounds lengthened with 1 to 3 ethylene oxide and/or propylene oxide units, as they are mentioned in DE-A-2 816 823, are well suited. Mixtures of the monomers mentioned can also be used. Methacrylates such as bis-GMA, HEMA, TEGDMA, Plex 6661 and acid methacrylates, such as 4-META are especially suited.

Aerosils (Aerosil 200, COK B4 from Degussa), quartzes, glasses, especially deactivated or non-basic glasses, precipitating silicic acids (HDKH), for example, are suitable fillers.

Suitable stabilizers include radical catchers such as substituted or non-substituted hydroxy aromatics compounds, especially methoxyphenol or Jonol, HALS (Hindered Amine Light Stabilizers), heavy metal catchers, such as EDTA and soluble sulfates.

With the ion-emitting substances, those are preferred which enable the release of fluoride ions, such as fluoride salts of the first or second main group such as sodium fluoride or calcium fluoride, or complex fluoride salts, such as KZnF$_3$, or as they are described in EP-A 0 717 977, fluoride-emitting glasses as well as mixtures of these fluoride ion sources.

Chlorohexidine, pyridinum salts or the usual pharmaceutical substances, such as β-lactame antibiotics (penicillins), cephalosporins, tetracyclines, ansamycins, kanamycins, chloramphenicol, fosfomycin, antibacterial macrolides, polypeptide antibiotics, chemotherapeutics such as sulfonamides, dihydrofolate reductase inhibitors, nitrofuran derivatives or gyrase inhibitors, for example, can be used as bactericidally or antibiotically active substances.

For the selection and implementation of the activity-terminating mechanism, it is basically decisive which enzyme is used for the proteolytic modification of collagen.

Some preferred embodiments are mentioned below, which basically explain implementation of the invention, whereby these embodiments are also not to be understood in any way as limiting or restricting for the invention.

One possibility for implementing the invention is altering the pH value of the "operating environment" of the proteases.

If one uses, for example, a clostridiopeptidase A from *Clotridium histolyticum* with a pH optimum around 7.0, then the activity of the proteases used can be ended by reducing the pH value by, for example, the addition of acids to the mixture used.

In another embodiment, the enzyme can, for example be applied in or with a neutral primer and will be coated with the acidic bond after the necessary penetration time.

A further embodiment is, for example, in the use of acid-forming photopolymerization initiators, as they are described in WO-98/47046 or in DE-A-197 36 471 and DE-A-197 43 564. These are activated by a light exposure step and thus take care of a reduction of the pH value.

If acid-sensitive proteases are used, then the pH reduction necessary for terminating the activity should, proceeding from the optimal pH of the respective protease or protease mixture, take place until the activity termination is reached.

This can be reached in one, two, three, four, five, six, seven or eight pH steps. Which pH steps are preferred or especially preferred depends upon the protease or protease mixture respective brought into use (A. J. Barrett, N. D. Rawlings, J. F. Woessner, *Handbook of Proteolytic Enzymes*. San Diego, Academic Press, 1998).

On the other hand, one can also, for example, use enzymes operating in an acid pH environment, such as pepsin. Since these operate at a pH value from 1 to 5, they can be used directly in the acid bonding composition.

"Shutting off" the protease activity takes place by neutralization of the acid components in the bonding by the hydroxyl apatite component of the dentine. The pH switch here leads on the one hand to an activity termination of the pepsin and on the other hand, pepsin is irreversibly deactivated at a pH greater than 7 (A. J. Barrett, N. D. Rawlings, J. F. Woessner, *Handbook of Proteolytic Enzymes*. San Diego, Academic Press, 1998, p. 810).

With this type of embodiment of the invention, it is possible with the use of a defined protease to deduce what kind of pH change is required in order to attain the activity termination. A further possibility of embodying the invention lies in the local restriction of the action of the protease. This can take place, for example, in the derivatization of the protease with large molecules such as agarose (for example, Sigma-Aldrich, Deisenhofen, 1999 catalogue, P3286) or by coupling the proteases to fillers generally used in bonding, such as quartzes, glasses or silica gels (production of the enzyme derivatives, for example, according to J. Chem. Technol. Biotechnol., 1992, 54 (3), 215–21). Basically any derivatization, which reduces the diffusion of the protease, is suited.

The reduction of the diffusion can, but need not, be combined with an activity-terminating mechanism. A proteolytically active protease can remain in the hybrid layer or in the adhesive bond between the dental hard substance and the dental material if it is assured through a diffusion inhibition that the protease with its proteolytic activity cannot penetrate into deeper layers. It is advantageous if the protease is prevented from penetrating uncontrolled into deeper layers of the dental hard substance.

A further possibility of locality-specific fixation of the protease used is the incorporation of proteases into the polymer matrix of the primer and/or the bond.

For example, here the derivatization with monomer molecules, which are capable of entering into a chemical bond with the molecules of the primer and/or bonding matrix, is possible. This can be attained in radically polymerized systems for example by modification of the proteases with methacrylic acid derivatives.

An addition or condensation through functional groups of the proteases themselves, for example through NH$_2$, SH, COOH or C—C double bonds, is also conceivable, however. With cationic systems, for example, the addition of, for example, NH$_2$ or SH groups directly to an epoxide monomer of the matrix, is also possible so that a derivatization of the actual protease is not even necessary. It is advantageous if the protease is chemically bound into the polymer matrix.

The place-specific fixation of the protease by chemical bonding into the polymer matrix can, but need not, be combined with an activity-terminating mechanism. A proteolytically active protease can remain in the hybrid layer or in the adhesive union between dental hard substance and dental material if it is assured through the chemical bonding into the polymer matrix that the protease cannot penetrate into deeper layers with its proteolytic activity. It is advantageous if the protease is prevented from penetrating uncontrolled into deeper layers of the dental hard substance.

A further possibility for implementing the activity termination of the proteases used is to briefly increase the temperature, which is not harmful for the dental hard substance. This can take place, for example, by the administration of energy from an external source (by way of example, usual heat sources, customarily used polymerization lamps, such as Elipar Trilight (Espe company, Seefeld), but also plasma lamps or lasers or electromagnetic radiators, or ultrasound, but also by generating chemical energy, such as the heat of polymerization of a subsequently applied filler material.

Another possibility of activity termination lies in the addition of redox-active substances. These are, for example, activated by light exposure of the primer/bonding/sealer and then destroy the proteases chemically. Let radical formers as typical radical-forming initiators be mentioned as examples for these redox-active substances. These are described in the literature (for example, J.-P. Fouassier, Photoinitiation, Photopolymerization and Photocuring. Munich, Vienna, New York: Hanser Publishers, 1995 or also J.-P. Fouassier, J. F. Rabek, ed., Radiation Curing in Polymer Science and Technology, Vol. II, Elsevier Applied Science, London, New York, 1993). These can be activated through UV or visible light, as for example benzoin alkyl ether, benzil ketals, acyl phosphinoxides or aliphatic and aromatic 1,2-diketone compounds, for example, camphor quinone, whereby the catalytic activity can be accelerated by the addition of activators, such as tertiary amines or organic phosphites in an inherently familiar manner.

Suitable initiator systems for triggering the radical polymerization through a redox mechanism are, for example, the peroxide/amine, peroxide/barbituric acid derivatives, or peroxide/acids systems. When using such initiator systems, it is appropriate to keep an initiator (for example, peroxide) and a catalyst component (for example, amine) separately. The two components are then homogeneously mixed with each other shortly before application.

A further possibility for activity termination lies in the inhibition of enzyme activity-deciding groups, substances or cofactors.

For example, metals from metallopeptidases can be complexed through, for example, typical complexing agents, such as chelating agents, such as EDTA or its salts. With this embodiment of the invention, it is important that the affinity of the added complexing agent to the target metal be higher than that of the protease to the metal. Preferred are complexing agents with a high activity toward bivalent cations, especially preferably those with a high affinity toward zinc, cobalt, iron or manganese. The complexing agents are used at least in equimolar amounts. If the metallopeptidases used contain two cocatalytically acting metal ions (cobalt and manganese-based and some of the zinc-based metallopeptidases), then the complexing agents can be used for better action in a molar ratio of two to one calculated on the metal ions.

A further possibility for inhibiting these proteases lies in the addition of ions, which form barely soluble salts with the ions mentioned, such as hydroxy, sulfide, phosphate, sulfate or carbonate ions.

Another activity termination is possible with such proteases, the catalytic activity of which is dependent upon the activity of thiophene groups or hydroxyl groups. Here it is possible through typical oxidation agents or through covalent modification, for example, alkylating agents, to obtain a termination of the proteolytic activity of the proteases.

It is also possible to attain an activity termination by administering commercially available protease inhibitors or their mixtures, such as Pepstatin A (Sigma-Aldrich company, Deisenhofen, 1999 catalog).

In this embodiment of the invention, the protease inhibitor mixture is brought into contact with the protease or protease mixture following sufficient penetration time of the protease or protease mixture used and likewise left on the dental hard substance.

A further possibility for minimizing activity is the subsequent use of a further enzyme, which is not in a position to cut up or modify collagen. This further enzyme must then be in a position to deactivate the collagen-degrading or collagen-modifying enzyme.

Proteases can either be applied in a separate step or be used preferably directly in the sealers or bondings or also primers or conditioners. Of course, a combination of the embodiments shown above is also possible. Likewise a chemical and/or physical activity termination in the sense of a denaturing of the enzyme is possible through generally known methods, such as, for example, acid precipitation, salting out, heat precipitation, solvent coagulation or structure alteration (equivalent in the sense of what has been said) or coagulation through heavy metal addition.

If the proteases are used in a separate solution, then the solutions have by way of example a concentration from 0.001 mg/ml to 10 mg/ml, preferably from 0.001 mg/ml to 1 mg/ml, especially preferably from 0.01 mg/ml to 0.2 mg/ml.

All aqueous and organic solvents can be used as solvents, which do not impair the activity of the enzymes to the extent that their use in accordance with the invention is rendered impossible. Preferable are aqueous solutions with or without buffer systems such as de-ionized water, phosphate buffers, tris buffers and glycine buffers. Solvents such as dialkyl ketones (for example, acetone, methyl-ethyl ketone), acetyl acetone or alcohols (for example, ethanol, propanol) or low viscosity polymerizable substances such as 2-hydroxyethyl methacrylate or (2,3-epoxy propyl)-methacrylate as well as mixtures of these are also suitable.

If the enzymes are used directly in the sealant or in the bonding, then the solutions have, for example, a concentration from 0.001 mg/ml to 20 mg/ml, preferably from 0.001 mg/ml to 1 mg/ml, especially preferably from 0.01 mg/ml to 0.2 mg/ml.

DETAILED DESCRIPTION OF THE EMBODIMENTS

Figure 1:
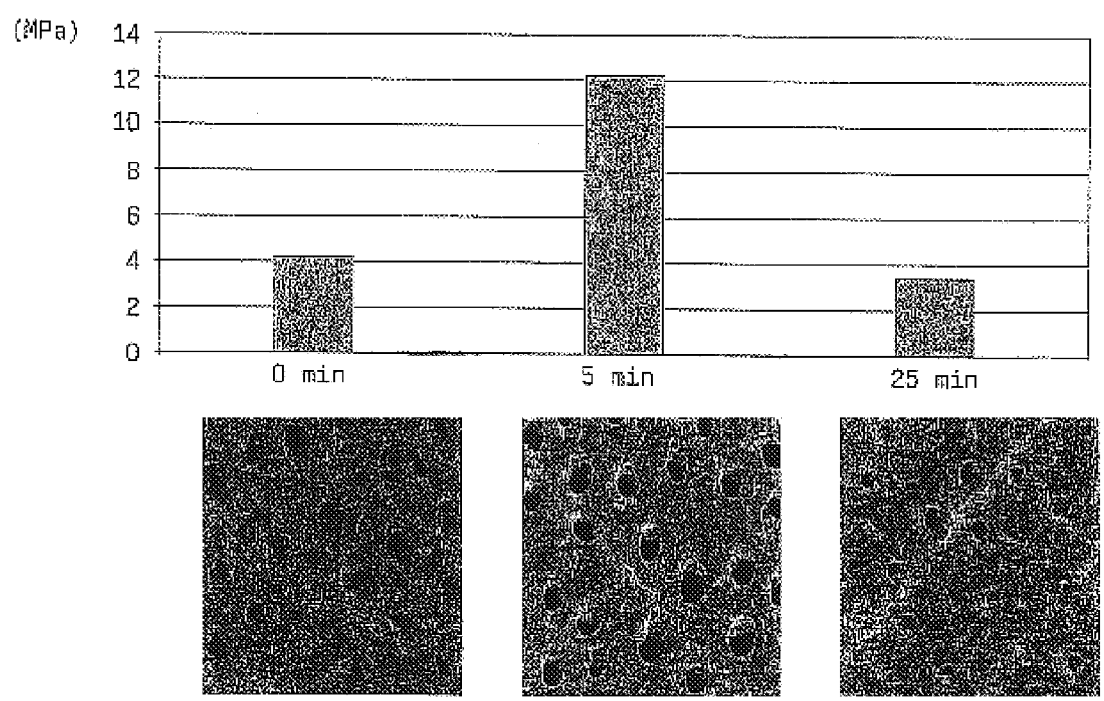
FIG. 1 shows mean adhesion values ascertained for adhesion experiments on bovine dentine. Under each result bar, a REM record of the dentine surface arising in connection with the treatment is illustrated.

The invention will be described below in greater detail on the basis of examples.

Preparation of Bovine Teeth

For each experiment, five bovine teeth frozen after extraction are thawed out, cleansed of remaining gum, and the roots are separated by sawing with a diamond saw. The still remaining pulp is removed with the aid of a pulp needle and the teeth are then rinsed with tap water. Level dental surfaces are obtained by labial polishing the teeth on a water-cooled diamond polishing machine. The teeth are then embedded in silicon such that the polished surface, which is kept quite moist, faces upward and is only then polished once again with a fine silicon carbide grinding paper. Then a wax platelet is glued to each tooth, which has a punchedout area of 6 mm in diameter (test field). The testing bodies so obtained are etched for 20 seconds relying on the typical process in practice ("all etch technique") by means of a typical phosphoric acid solution (Minitip® etching gel, ESPE Dental AG company, Seefeld) and subsequently thoroughly rinsed with water.

Embodiment 1

Activity Termination through pH Alteration

Bovine teeth were prepared in accordance with the procedure described above. Subsequently in an aqueous solution 20 µg of collagenase from *Clostridium histolyticum* Type 1a (Sigma-Aldrich company, Deisenhofen, 1999 catalog) in 5 µl of de-ionized water is applied to the test field and evenly distributed. Following five minutes of incubation, the acid Pertac Universal Bond (ESPE Dental AG company, Seefeld) was applied according to manufacturer's directions and hardened according to manufacturer's instructions. Subsequently the bonding layer is covered with 50 µl of de-ionized water. After one hour, 40 µl of the sample on the bonding layer is taken up with a pipette and transferred to a reagent solution for determination of collagenase activity. 50 µg of fluorescence-marked gelatin (Molecular Probes company, Göttingen) was situated in 960 µl of disodium hydrogen phosphate solution (pH 7.0; 100 mM). The presence of collagenase activity is observable on the increase in fluorescence. The excitation wave length was 495 nm according to manufacturer's instruction and fluorescence emission was measured at 515 nm in a fluorescence photometer of the Kontron company (SFM 25), in accordance with the manufacturer's instructions. No collagenase activity could be measured.

By coating the collagenase with an acid bonding, the activity of the enzyme, which has a pH optimum in the pH 7 range, is deactivated.

In a control experiment, 20 µg of collagenase in 50 µl of disodium hydrogen phosphate solution (pH 7.0; 100 mm) was applied to a hardened bonding layer. Collagenase activity was determined after one hour. Within one minute, relative fluorescence increased by more than 100%. In a further control experiment, the hardened bonding layer was coated directly with 50 µl of fluorescence-marked gelatin solution. No collagenase activity could be detected.

The acidification caused by the Pertac Universal Bond terminated the collagenase activity.

Embodiment 2

Activity Termination through pH Alteration 2.5 ml of a pepsin solution (10 µg/ml) in a 20 mM disodium hydrogen phosphate buffer (pH 2.0) were added to 1 g of ground bovine dentine and allowed to remain there for 20 min. under agitation. Subsequently the mixture was centrifuged for 1 min. in a Heraeus Biofuge Pico at 10,000 rpm. 900 µl of the residue were mixed with 12 µg of fluorescence-marked casein (Molecular Probes company, Göttingen) in 100 µl 20 mM of disodium hydrogen phosphate buffer (pH 2.0). The presence of proteolytic pepsin activity is manifested in the increase in fluorescence with an excitation wave length of 480 nm and with an emission wave length of 510 nm. The measurements showed that through the alkalizing action of the dentine, the pH was shifted so far into the alkaline that no pepsin activity was determinable any more.

Embodiment 3

Activity Inhibition through Diffusion Inhibition

Agarose-coupled pepsin was used, commercially obtainable at the Sigma-Aldrich company, Deisenhofen. 10 µg of this was added to the aqueous phase of Prompt L-Pop (ESPE Dental AG, Seefeld). The aqueous phase was mixed with the second component of the bonding according to manufacturer's directions. The mixture was transferred to a 96 microtiter plate and hardened with an Elipar Highlight illumination unit (ESPE Dental AG company) by light polymerization (40 sec).

The bonding layer was coated with 100 µl of disodium hydrogen sulfate buffer (50 mM, pH 2.0), containing 5 µg of fluorescence-marked casein (Molecular Probes company). After 30 min, 90 µl was removed from the bonding surface with a pipette and mixed with 110µl of the disodium hydrogen phosphate buffer. The fluorescence increase was measured at 510 nm emission (excitation at 480 nm). The increase in relative fluorescence by 30% indicated that proteolytically active pepsin was present on the surface of the bonding layer.

It was consequently shown that the enzyme can remain active, but the mobility of the enzyme is restricted by coupling to agarose, and the enzyme consequently cannot travel into deeper layers of the dentine.

In a control experiment, the hardened pepsin/bonding layer (Prompt-L-Pop, ESPE Dental AG, Seefeld) was coated with 100 µl disodium hydrogen phosphate buffer (50 mm, pH 2.0). After 30 min, 90µl was taken from the bonding surface with a pipette and mixed with 110µl of the disodium hydrogen phosphate buffer containing 5µg of fluorescence-marked casein (Molecular Probes company). The relative fluorescence was determined at 510 nm emission (excitation at 480 nm). In comparison with the control sample, which contained 5 µg of fluorescence-marked casein in 200µl of measuring solution, no increase in fluorescence could be observed. This confirmed that agarose-coupled enzyme cannot leave the hardened bonding layer.

Embodiment 4

The preparation of the bovine teeth and the test fields on the bovine teeth were described under "Bovine Teeth Preparation." EBS-Multi from ESPE Dental AG company, Seefeld, contains, besides an etching gel, a primer solution and a bonding solution. 1 mg collagenase from *Clostridium histolyticum* Type 1a (Sigma-Aldrich company, Deisenhofen, 1999 catalog) was dissolved in 1 ml of primer solution. The EBS-Multi bonding was introduced into the test field according to directions, whereby the primer was used comparatively with collagenase and without collagenase. Subsequently a Pertac filler (ESPE Dental AG company, Seefeld) was introduced according to manufacturer's directions. After 24 hour storage at 36° C. and 100% humidity, the wax platelets were removed and the test body was drawn in a tensile test (Zwick Universal Testing Machine).

The mean adhesive value for 5 bovine teeth, which was obtained with the primer variant without collagenase, came to 3.96 MPa with a standard deviation of 31%. The mean adhesive value, which was attained with the primer variant with collagenase, came to 10.5 MPa with a standard deviation of 8.7%.

By integrating the collagenase in the primer system, the adhesive values could consequently be increased significantly and the standard deviation of the adhesion values could be diminished.

Embodiment 5

The preparation of bovine teeth and the test fields on the bovine teeth was described under "Bovine Teeth Preparation." Prompt L-Pop (ESPE Dental AG company, Seefeld) consists of an aqueous phase and a polymer-monomer phase, which are kept in separate chambers in a blister packaging.

The liquid is withdrawn from a series of blisters. The aqueous phase was enriched with pepsin up to a concentration of 5 mg per ml. The aqueous phase and polymer-monomer phase were mixed in a proportion of 1:5 so that the end concentration of 1 mg of pepsin per ml of bonding was reached.

The Prompt L-Pop bonding was introduced into the test field according to directions, whereby for comparison the aqueous phase was used once with and once without pepsin additive. Subsequently, a Hytac filler (ESPE Dental AG company, Seefeld) was introduced following the manufacturer's directions. After 24 hour storage at 36° C. and 100% air humidity, the wax platelets were removed and the test body was drawn in a tensile experiment (Zwick Universal Testing Machine).

The mean adhesion value of 5 bovine teeth, which was obtained with the Prompt L-Pop variant without pepsin, came to 4.1 MPa with a standard deviation of 39%. The mean adhesion value of 5 bovine teeth, which was obtained with the Prompt L-Pop variant with pepsin, came to 5.9 MPa with a standard deviation of 9%.

Through the integration of pepsin into a bonding, the adhesion values could consequently be increased significantly and the standard deviation of the adhesion values could be diminished.

Comparison Examples

In the first experiment, the bovine teeth were subjected to the bonding and filling process described below without further treatment steps. Then the examination of the adhesive union took place through an adhesion drawing experiment with a Zwick Universal Testing Machine.

In the second experiment, the bovine teeth were treated with a collagenase solution. A commercially obtainable collagenase from Clostridium histolyticum Type 1a (Sigma-Aldrich company, Deisenhofen, 1999 catalog) was used. 50 $\mu$g of collagenase in 50 $\mu$l of disodium hydrogen phosphate buffer (pH 7.0; 50 mM) were applied on each bovine tooth by means of pipette into the testing field. After five minutes of incubation, the collagenase solution was thoroughly rinsed. The bonding and filling procedure described below took place, followed by the examination of the adhesive union by an adhesion drawing experiment with a Zwick Universal Testing Machine.

In a third experiment, the bovine teeth were subjected to the same process as described in the second experiment. This time the incubation time came to 25 min.

Bonding and filling procedure

The EBS-Multi® bonding (ESPE Dental AG company, Seefeld) was introduced into the test field according to directions and subsequently a filler with Hytac® (ESPE Dental AG company, Seefeld) was introduced according to manufacturer's directions. After 24 hour storage at 36° C. and 100% air humidity, the wax platelets were removed and the test body was drawn in a tensile experiment (Zwick Universal Testing Machine). The mean dentine adhesion values ascertained for in each case of the five bovine teeth can be gathered from Illustration 1.

Legend to Illustration 1

The mean adhesion values ascertained for adhesion experiments on bovine dentine are indicated on the Y axis in MPa. The X axis is subdivided corresponding to three experiments conducted according to incubation times with the collagenase solution. 0 min: no collagenase incubation; 5 min: collagenase incubation for 5 min; 25 min: collagenase incubation for 25 min. Under each result bar, a REM record of the dentine surface arising in connection with the treatment is illustrated.

X-ray electron microscope examination

In any given case a bovine tooth was processed according to the procedures described for experiments one, two and three. The bonding and filling procedures were not conducted. The teeth were dried and spattered with a device from Balzers Union company. Subsequently the treated bovine dentine surfaces were microscopically examined with an REM device from Hitachi company. Illustrations of the surfaces are to be seen in Illustration 1 in a 1000 times enlargement.

What is claimed is:

1. A process for treating a surface of a tooth, comprising:
   applying a surface treatment composition comprising a collagen-degrading enzyme and a material that inhibits the activity of said collagen-degrading enzyme to the tooth surface; and leaving the surface treatment composition on the tooth.

2. A process according to claim 1, wherein the material that inhibits the activity of said collagen-degrading enzyme is selected from the group consisting of acids, bases, buffers, polymerizable substances, salts, radical-binding substances, oxidizable or reducible substances, protease inhibitors, non-collagen-modifying enzymes, diffusion-inhibiting substances, and combinations thereof.

3. A process according to claim 1, wherein the collagen-degrading enzyme is selected from the group consisting of peptidases, peptidyl peptidases, dipeptidases, dipeptidyl peptidases, oligopeptidases, proteinases, endopeptidases, exopeptidases, serine peptidases, cysteine peptidases, aspartatepeptidases, and metallopeptidases.

4. A process according to claim 1, wherein the process for surface treatment includes the application of at least one material, selected from the group consisting of bonding, primer, conditioner, and filler material.

5. A process according to claim 1, wherein the surface treatment composition is produced prior to the surface treatment by mixing the collagen-degrading enzyme and the material that inhibits the collagen-degrading enzyme activity.

6. A process for the surface treatment of a tooth, comprising:
   applying a surface treatment composition comprising a collagen-degrading enzyme and optionally a material that inhibits the activity of said collagen-degrading enzyme activity to a tooth surface; and coating of the surface treatment composition with at least one material selected from the group consisting of bonding material, primer, acid, tooth conditioning material, and filler material, wherein the surface treatment composition remains on the tooth surface, and wherein activity of the collagen-degrading enzyme is inhibited by at least one of the material that inhibits the activity of said collagen-degrading enzyme and the at least one material selected from the group consisting of bonding material, primer, acid, tooth conditioning material, and filler material.

7. A process according to claim 6, wherein the collagen-degrading enzyme is selected from the group consisting of peptidases, peptidyl peptidases, dipeptidases, dipeptidyl peptidases, oligopeptidases, proteinases, endopeptidases, exopeptidases, serine peptidases, cysteine peptidases, aspartate peptidases, and metallopeptidases.

8. A process according to claim 6, wherein the activity of the collagen-degrading enzyme is inhibited by formation of radicals.

9. A process according to claim 6, wherein the activity of the collagen-degrading enzyme is inhibited by changing a pH value.

10. A process according to claim 6, wherein the activity of the collagen-degrading enzyme is inhibited by at least one of temperature, salt concentration, solvent, redox potential, a modification of the catalytic group of the enzyme, addition of protease inhibitors, bonding the enzyme to diffusion-inhibiting substances, polymerization into these diffusion-inhibiting substances, and addition of non-collagen-modifying enzymes.

* * * * *

UNITED STATES PATENT AND TRADEMARK OFFICE
CERTIFICATE OF CORRECTION

PATENT NO. : 6,752,989 B1
DATED : June 22, 2004
INVENTOR(S) : Haeberlein, Ingo

It is certified that error appears in the above-identified patent and that said Letters Patent is hereby corrected as shown below:

Title page,
Item [56], References Cited, OTHER PUBLICATIONS,
"V. I. Deribas, et al.," reference, delete "immoblilised" and insert -- immobilised --, therefor.
"A. Bahn, et al.," reference, insert -- " -- before "Enzymatic"; and after "Layer" insert -- " --.
Item [57], ABSTRACT,
Line 1, delete "The invention concerns" and insert -- A --, therefor.
Line 1, delete "agents" and insert -- agent --, therefor.
Line 2, delete ", including" and insert -- includes --, therefor.
Line 4, after "during" delete "the".

Drawings,
Figure 1, line 6, delete "B" and insert -- 8 --, therefor.

Column 7,
Lines 28 and 30, delete "J.-P." and insert -- J. P. --, therefor.

Signed and Sealed this

Twenty-ninth Day of November, 2005

JON W. DUDAS
*Director of the United States Patent and Trademark Office*